(12) United States Patent
Mizukoshi et al.

(10) Patent No.: US 9,482,648 B2
(45) Date of Patent: Nov. 1, 2016

(54) METHOD FOR DETECTING GALACTO-OLIGOSACCHARIDE

(71) Applicant: KABUSHIKI KAISHA YAKULT HONSHA, Minato-ku, Tokyo (JP)

(72) Inventors: Harumi Mizukoshi, Tokyo (JP); Kazumasa Kimura, Tokyo (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 0 days.

(21) Appl. No.: 15/025,193

(22) PCT Filed: Sep. 26, 2014

(86) PCT No.: PCT/JP2014/075718
§ 371 (c)(1),
(2) Date: Mar. 25, 2016

(87) PCT Pub. No.: WO2015/046463
PCT Pub. Date: Apr. 2, 2015

(65) Prior Publication Data
US 2016/0238572 A1  Aug. 18, 2016

(30) Foreign Application Priority Data

Sep. 30, 2013 (JP) ................. 2013-205503

(51) Int. Cl.
*G01N 30/06* (2006.01)
*G01N 33/02* (2006.01)
*G01N 33/14* (2006.01)
*G01N 30/88* (2006.01)

(52) U.S. Cl.
CPC ............. *G01N 30/06* (2013.01); *G01N 30/88* (2013.01); *G01N 33/02* (2013.01); *G01N 33/143* (2013.01); *G01N 2030/067* (2013.01); *G01N 2030/8836* (2013.01); *Y10T 436/143333* (2015.01)

(58) Field of Classification Search
CPC ...... G01N 30/02; G01N 30/04; G01N 30/06; G01N 30/861; G01N 30/8675; G01N 30/8679; G01N 30/88; G01N 33/02; G01N 33/04; G01N 33/14; G01N 33/143; G01N 33/66; G01N 2030/067; G01N 2030/8836; Y10T 436/143333

USPC .................. 436/20, 22, 23, 94, 161; 422/70; 435/14; 210/656, 198.2
See application file for complete search history.

(56) References Cited

U.S. PATENT DOCUMENTS

2005/0186679 A1* 8/2005 Viskov ................ B01D 15/363
   436/94
2009/0023171 A1  1/2009 Viskov et al.

FOREIGN PATENT DOCUMENTS

| JP | 2007523352 A | 8/2007 |
| JP | 2008170428 A | 7/2008 |
| WO | 2005080438 A1 | 9/2005 |

OTHER PUBLICATIONS

De Slegte, Determination of trans-Galactooligosaccharides in Selected Food Products by Ion-Exchange Chromatography: Collaborative Study, Journal of AOAC International, Mar. 2002, pp. 417-423 (7), vol. 85, No. 2.

Harumi Mizukoshi et al., "PMP Yudotaikaho 0 Mochiita Koso Bunkai to HPLC ni yoru Shokuhinchu no Galacto-oligosaccharide no Teiryo" Journal of Applied Glycoscience, 2005, vol. 52, suppl., p. 44 (C1p-9).

International Search Report (ISR) mailed Dec. 22, 2014, issued for International application No. PCT/JP2014/075718.

Kazumasa Kimura et al., "Studies on the natural galacto-oligosaccharide in commercial cow's milk", Annual Report of Yakult Central Institute for Microbiological Research, 1997, No. 17, p. 1-7.

* cited by examiner

*Primary Examiner* — Maureen Wallenhorst
(74) *Attorney, Agent, or Firm* — Law Office of Katsuhiro Arai (57) ABSTRACT

A method for detecting and quantifying galacto-oligosaccharide in a sample containing galacto-oligosaccharide and dextrin is characterized in that the sample is caused to react with a derivatizing reagent to derivatize the dextrin and galacto-oligosaccharide in the sample, after which the galacto-oligosaccharide component in the sample is separated by high-performance liquid chromatography using a C30 reverse-phase chromatography column, thereby accurately detecting and quantifying galacto-oligosaccharide with ease and at low cost.

9 Claims, 10 Drawing Sheets

FIG. 1

HPLC Chromatogram Using Gel Filtration Column

FIG. 2

PMP Derivative - Reverse-phase HPLC Chromatogram (C30)

FIG. 3

PMP Derivative - Reverse-phase HPLC Chromatogram (C18 Reverse-phase Column)

FIG. 4

PMP Derivative - Reverse-phase HPLC Chromatogram (C8 Reverse-phase Column)

PMP Derivative - Reverse-phase HPLC Chromatogram (C30)
Potassium phosphate buffer solution (pH5)/$CH_3CN$ (79/21)

PMP Derivative - Reverse-phase HPLC Chromatogram (C30)

METHOD FOR DETECTING GALACTO-OLIGOSACCHARIDE

This application is the U.S. National Phase under 35 U.S.C. §371 of International Application PCT/JP2014/075718, filed Sep. 26, 2014, which claims priority to Japanese Patent Application No. 2013-205503, filed Sep. 30, 2013. The International Application was published under PCT Article 21(2) in a language other than English.

TECHNICAL FIELD

The present invention relates to a method for detecting and quantifying galacto-oligosaccharide in a sample containing galacto-oligosaccharide and dextrin.

BACKGROUND ART

Galacto-oligosaccharide is a mixture of oligosaccharides, each constituted by galactose as a primary component and having a different bonding mode, and is generally manufactured by causing lactose to undergo transitional reaction using β-galactosidase. Galacto-oligosaccharide has been reported to have physiological benefits such as increasing the bifidobacteria in the intestines to regulate the enteric environment, and reducing mesenteric fat and thereby contributing to the prevention of adult diseases, and for some time has been found useful as a food for specified health use, functional food, or material thereof. If galacto-oligosaccharide is used as a component of food for specified health use, etc., quantitative analysis data must be displayed to guarantee its quality, compliance with standards, and use as a functional component, and accordingly there is a need for establishing a highly accurate quantification method.

One method to quantify galacto-oligosaccharides in beverages or food is to add β-galactosidase to act upon galacto-oligosaccharide, quantify the galactose produced as a result of enzyme decomposition, and calculate the quantity of oligosaccharide (Non-patent Literature 1). However, detecting the galactose being produced requires anion-exchange high-performance liquid chromatography fitted with an expensive pulse-type electrochemical detector, which keeps the general utility of this method low. Also, when the beverage or food contains lactose or other nutritional components, the galactose produced by enzyme treatment cannot be discriminated from the galactose separating from lactose, which consequently reduces the quantification accuracy of galacto-oligosaccharide.

Another method is available, whereby a characteristic component in galacto-oligosaccharide, such as 4'-galactosyl lactose (4'-GL; Galβ1-4Galβ1-4Glc), is quantified and the total quantity of galacto-oligosaccharide is calculated back from the quantity of 4'-GL. This method is particularly effective when the content of 4'-GL in the galacto-oligosaccharide to be used is known and this content is stable from one lot to another. For quantifying 4'-GL in a beverage or food sample, conventionally a method to separate other components in the beverage or food from 4'-GL by gel filtration chromatography based on molecular size is primarily used.

As mentioned above, however, galacto-oligosaccharide is often used as a functional material in nutrient-rich beverages and foods such as formulated powdered milk for infants and fermented milk products, and in many cases these beverages and foods contain sugar sources whose molecule is equivalent in size to that of 4'-GL, in which case these sugar sources cannot be separated from 4'-GL by gel filtration chromatography. For example, an attempt to separate and quantify 4'-GL in beverages or food containing maltotriose, which is a type of sugar contained in dextrin, by gel filtration chromatography would result in overlapping peaks from the two substances that have eluted from the column because maltotriose has the same molecular size as 4'-GL, thus affecting the quantification of 4'-GL or specifically the quantification of galacto-oligosaccharide.

Among the methods to detect oligosaccharide by reverse-phase chromatography, one that uses a C8 or C18 reverse-phase chromatography column is known (Patent Literature 1). However, an attempt to separate galacto-oligosaccharide in beverages or food using such column would fail to separate the galacto-oligosaccharide component from other components in the beverage or food.

BACKGROUND ART LITERATURE

Patent Literature

Patent Literature 1: Published Japanese Translation of PCT International Patent Application No. 2007-523352

Non-Patent Literature

Non-patent Literature 1: Journal of AOAC International, Volume 85, Number 2, March 2002, pp. 417-423(7)

SUMMARY OF THE INVENTION

Problems to be Solved by the Invention

Accordingly, an object of the present invention is to provide a method for accurately quantifying 4'-GL and galacto-oligosaccharide by separating 4'-GL with ease and at low cost from a sample containing galacto-oligosaccharide and dextrin.

Means for Solving the Problems

After studying in earnest to achieve the aforementioned object, the inventors of the present invention completed the present invention after finding that, by causing a sample containing galacto-oligosaccharide and dextrin to react with a derivatizing reagent to derivatize the dextrin and galacto-oligosaccharide in the sample, and then putting the result through high-performance liquid chromatography using a C30 reverse-phase chromatography column, the galacto-oligosaccharide component in the sample can be sufficiently separated.

In other words, the present invention is a method for detecting and quantifying galacto-oligosaccharide, which provides a method for detecting and quantifying galacto-oligosaccharide in a sample containing galacto-oligosaccharide and dextrin, characterized in that the sample is caused to react with a derivatizing reagent to derivatize the dextrin and galacto-oligosaccharide in the sample, after which the galacto-oligosaccharide component in the sample is separated by high-performance liquid chromatography using a C30 reverse-phase chromatography column.

Effects of the Invention

According to the detection and quantification method proposed by the present invention, galacto-oligosaccharide and other components in the sample can be separated with ease and at low cost to allow for accurate quantification of galacto-oligosaccharide. By using the method proposed by the present invention to detect and quantify galacto-oligosaccharide in beverages, food, etc., the quantity of galacto-oligosaccharide contained in the beverage, food, etc., can be accurately managed to enable quality assurance, while also allowing for accurate acquisition and display of various effectiveness test data, etc.

MODE FOR CARRYING OUT THE INVENTION

The detection and quantification method proposed by the present invention is such that galacto-oligosaccharide contained in a sample of a beverage, food, etc., is derivatized and then the result is put through high-performance liquid chromatography (HPLC) using a C30 reverse-phase chromatography column, thereby separating galacto-oligosaccharide from other components in the sample and quantifying the separated galacto-oligosaccharide. Galacto-oligosaccharide is a mixture of disaccharide to hexasaccharide whose molecule contains one or more molecules of galactose, expressed by the general formula Gal-(Gal)n-Glc (wherein Gal represents a residual galactose group, Glc represents a residual glucose group, and n is an integer of 0 to 4). It should be noted that lactose is not contained in galacto-oligosaccharide.

The primary component of galacto-oligosaccharide is a trisaccharide 4'-galactosyl lactose (4'-GL), comprising lactose and one galactose bound to its non-reducing end. Other specific components include Galβ1-3Glc, Galβ1-2Glc, Galβ1-6Glc, Galβ1-6Galβ1-4Glc, Galβ1-6Galβ1-4Galβ1-4Glc, and Galβ1-4Galβ1-4Galβ1-4Glc, or the like. Under the detection and quantification method proposed by the present invention, galacto-oligosaccharide can be detected and quantified as a mixture, or an individual galacto-oligosaccharide component may be detected and quantified; from the viewpoint of quantification accuracy, however, preferably 4'-GL is separated and then detected and quantified, followed by back-calculating the obtained quantity to determine the total quantity of galacto-oligosaccharide.

Galacto-oligosaccharide may be obtained in any way; for example, galacto-oligosaccharide produced by means of transitional reaction using lactose as the material, and lactose decomposition enzyme (β-galactosidase), can be used. During the transitional reaction, a microorganism that produces enzyme may be added to act upon the material. Examples of materials containing lactose include commercially available lactose, milk, powdered milk, cheese whey, or the like. The enzyme used is not limited in any way and any enzyme may be used so long as it can derive galacto-oligosaccharide, where examples include enzymes that can hydrolyze lactose in the material and cause the galactose produced by decomposition to transition to lactose or glucose, specifically β-galactosidase or α-galactosidase. These enzymes may be used alone or two or more of them may be combined for use. The enzyme treatment conditions are not limited in any way, and generally an appropriate range of concentration of material is 10 to 70%, that of pH is 3 to 8, that of concentration of enzyme is 0.01 to 100 units/ml, that of temperature is 20 to 70° C., and that of reaction time is 2 hours to 3 days. Commercially available galacto-oligosaccharide liquid sugar can also be used, such as Oligomate 55N (Yakult Pharmaceutical Industry). It is also possible to use galacto-oligosaccharide isolated from natural sources containing galacto-oligosaccharide and purified by a conventional method. The type of natural source containing galacto-oligosaccharide is not limited in any way, and milk from mammals can be used, for example.

Under the present invention, the sample used for detection and quantification of galacto-oligosaccharide is not limited in any way so long as it contains galacto-oligosaccharide and dextrin, and examples include food for specified health use, functional food, health food, nutritional supplement food, special food for infant/children/pregnant women/sick people, food for people having difficulty swallowing, formulated powdered milk for infants or other beverages, food, or material thereof, and pharmaceutical products, among others. Among these, preferably the method proposed by the present invention is applied to formulated powdered milk for infants containing a high content of sugar components, because it allows for detection and quantification of galacto-oligosaccharide with high precision. Dextrin is a general term that refers to substances comprising three or more glucose molecules polymerized together. One type of dextrin is maltodextrin, which is a polymer of D-glucoses polymerized together by α-1,4 bonding, has an equivalent dextrose weight of less than 20, and is obtained by hydrolyzing starch.

Maltodextrin includes maltotriose comprising three glucose molecules, tetrasaccharide comprising four glucose molecules polymerized together, and polysaccharide comprising more glucose molecules polymerized together. Maltotriose, comprising three glucose molecules polymerized together, has the same molecular weight and size as 4'-GL but its solid hydroxyl group structure is partially different. In cases where molecules of the same size as 4'-GL were present in a sample of a beverage, food, etc., conventional methods such as gel filtration chromatography could not separate 4'-GL and maltotriose to quantify galacto-oligosaccharide; by using the method proposed by the present invention, however, the two can be separated sufficiently. Equivalent dextrose weight is a representation of reducing sugar in the sample as glucose, obtained as a percentage of solid content. The maximum value of equivalent dextrose weight is 100, which indicates that all of the solid content is glucose. Equivalent dextrose weight is an indicator of rate of hydrolysis from starch, where dextrin of smaller equivalent dextrose weight, or specifically a lower rate of hydrolysis, contains more polysaccharide components. On the other hand, dextrin of greater equivalent dextrose weight, or specifically a higher rate of hydrolysis, contains more oligosaccharide components.

Under the detection and quantification method proposed by the present invention, first a derivatizing reagent is caused to react with the sample to derivatize the sugar in the sample. The derivatizing reagent is not limited in any way so long as it can derivatize galacto-oligosaccharide, where examples include hydrophobic derivatives capable of absorbing ultraviolet light or visible light or detecting fluorescent light, or specifically 1-phenyl-3-methyl-5-pyrazolone (PMP), 2-aminopyridine, 2-aminobenzamide, 3-aminoquinone, ethyl 4-amino benzoate, butyl 4-amino benzoate, and 4-trimethyl ammonium aniline, and any one type of derivative selected from the foregoing may be used. Particularly, PMP is preferably used for sufficient separation of galacto-oligosaccharide components.

In the case of derivatization by PMP, derivatization can be implemented by, for example, adding 0.5 M PMP methanol solution and 0.6 M NaOH solution to the sample to cause reaction for 30 minutes at 70° C., and then adding 0.1 M hydrochloric acid and chloroform to the reaction liquid to agitate the mixture, followed by removing the chloroform constituting the bottom layer. Although sugar such as galacto-oligosaccharide is hydrophilic, its derivatization by hydrophobic derivatizing reagent turns the derivatized part of sugar hydrophobic to remain longer in the column if it is fed to a high-performance liquid chromatography column containing alkyl groups in the stationary phase, compared to a hydrophilic component would.

After the derivatization treatment, the sample is put through high-performance liquid chromatography to separate the galacto-oligosaccharide component in the sample. Under the present invention, the column used for high-performance liquid chromatography is a C30 reverse-phase chromatography column, or specifically a column containing alkyl groups (triacontyl groups) of carbon number 30 in the stationary phase. This is because a column of carbon number 30 must be used in order to sufficiently separate galacto-oligosaccharide in the sample. More specific examples include Develosil RPAQUEOUS (Nomura Chemical), Develosil C30-UG (Nomura Chemical) and Inertosil C30 S-Select (GL Sciences). Among these, the column with a stationary phase containing cis alkyl groups having double bonds is preferred, or specifically Develosil RPAQUEOUS (Nomura Chemical) is preferred, from the viewpoint of separability of galacto-oligosaccharide. C30 reverse-phase chromatography columns are suitable for separating galacto-oligosaccharide, probably because the length and solid structure of alkyl groups are causing the retention time of galacto-oligosaccharide, maltotriose, etc., to change.

For the eluent that can be used for the mobile phase of high-performance liquid chromatography is not limited in any way so long as it does not negatively affect the column or apparatus, and examples include eluent constituted only by water, eluent constituted only by buffer solution, and mixed liquid of water or buffer solution and polar organic solvent, of which use of a mixed liquid of buffer solution and polar organic solvent is preferred. The mixing ratio (vol/vol, all mixing ratios are indicated in units of vol/vol hereinafter) of buffer solution and polar organic solvent is not limited in any way, but preferably the range of buffer solution/polar organic solvent is 79/21 to 80/20. This is because, by using eluent in this range, galacto-oligosaccharide is sufficiently separated and good chromatograms can be obtained. For a similar reason, the pH of buffer solution is preferably in a range of 4 to 8, or particularly preferably in a range of 5 to 6.

Also, preferably a mixed solution is used that contains, as the buffer solution, at least one type selected from potassium phosphate buffer solution, potassium citrate buffer solution, ammonium formate buffer solution, and potassium acetate buffer solution, and as the polar organic solvent, at least one type selected from acetonitrile, methanol, ethanol, propanol, and butanol, where use of a mixed solution of potassium phosphate buffer solution and acetonitrile is particularly preferred, the pH of potassium phosphate buffer solution is preferably in a range of 5 to 6, and the mixing ratio of potassium phosphate buffer solution and acetonitrile is preferably in a range of 79/21 to 80/20 based on potassium phosphate buffer solution/acetonitrile.

High-performance liquid chromatography can be implemented using a commercially available HPLC apparatus, and the column equilibration, flow rate, and various other conditions can be set as deemed appropriate based on the sample volume, etc. After the high-performance liquid chromatography, the obtained fraction can be detected and quantified using various detectors. For examples, an ultraviolet light absorbance detector, visible light absorbance detector, or other absorbance detector, any of various optical rotation detectors, or fluorescent light detector, etc., can be used. Under the present invention, use of an ultraviolet absorbance detector allows for simple and also accurate quantification.

For the method to detect and quantify galacto-oligosaccharide in the sample, the means described below can be used, for example. First, water or other solvent is added to a sample containing galacto-oligosaccharide whose 4'-GL content is known, to dissolve the sample, and then an appropriate quantity of internal reference substance is added to prepare a sample solution. Separately, the same galacto-oligosaccharide and internal reference standard substance are dissolved in water, etc., to prepare a standard test solution. The standard test solution is diluted in stages to prepare 10-times diluted solution, 20-times diluted solution and 40-times diluted solution, for example. Next, the sample solution and standard test solution are derivatized with a derivatizing reagent of PMP, etc. The derivatized sample solution and standard test solution are put through high-performance liquid chromatography, respectively, to obtain chromatograms using a detector. The conditions of high-performance liquid chromatography are as mentioned above.

The obtained result of standard test solution is used to create a calibration curve. For each of the standard test solutions diluted in stages, a calibration curve is obtained based on the least squares method, with the horizontal axis representing the content of galacto-oligosaccharide and the vertical axis representing the area ratio of 4'-GL and internal reference substance, which should give the following formula (calibration curve):

$$\text{Area ratio } (y) = \text{Constant } (a) \times \text{Galacto-oligosaccharide content } (x)$$

Next, the area ratio of 4'-GL and internal reference substance is calculated from the result of the sample solution and the area ratio is assigned to the above calibration curve, so that the content of galacto-oligosaccharide in the sample can be calculated. By putting the calculated result through supplemental calculations as deemed appropriate based on the dilution ratio, etc., of the sample in the pretreatment stage, accurate galacto-oligosaccharide content is quantified.

The present invention is described in greater detail below by citing examples, but it should be noted that the present invention is not limited by these examples in any way.

EXAMPLES

Comparative Example 1

Quantification of 4'-GL Using Gel Filtration Chromatography (1) Preparation of Sample Solution Formulated powdered milk for infants containing galacto-oligosaccharide liquid sugar (Oligomate 55N: Yakult Chemical Industry) at a ratio of 2.3 g/100 g based on galacto-oligosaccharide content as well as maltodextrin at a ratio of 1.5 g/100 g was weighed and 2.6 g thereof was weighed and dissolved by adding a small amount of warm water, after which the dissolved formulated powdered milk was let stand until it reached room temperature and then distilled water was added to prepare 20 ml of dissolved milk. Into a measuring flask, 4 ml of dissolved milk was introduced and then precisely 2 ml of aqueous solution containing internal reference substance by 0.1% was added, after which distilled water was added to make the total volume 20 ml, to obtain a sample solution (powdered milk 101 (GOS added)). The galacto-oligosaccharide content per 20 ml of dissolved milk was 2.6 g×2.3/100=0.0598 g, which means that the content per 100 ml was 0.299 g.

Formulated powdered milk for infants contains, as materials, lactose, whey protein digest, palm oil, whole powdered milk, fractionated palm kernel oil, refined soybean oil, galacto-oligosaccharide liquid sugar, casein calcium, maltodextrin (saccharified starch), refined fish oil, calcium carbonate, magnesium chloride, lecithin, potassium phosphate, potassium chloride, sodium phosphate, potassium hydroxide, lactoferrin, vitamin C, calcium chloride, iron pyrophosphate, taurine, vitamin E, zinc sulfate, cystine, sodium cytidylate, niacin, calcium pantothenate, vitamin A, copper sulfate, sodium inosinate, sodium uridylate, sodium guanylate, vitamin B1, 5'-AMP, vitamin B6, vitamin B2, folic acid, carotene, vitamin D, and vitamin B12, and the nutritional components of formulated powdered milk for infants are shown in Table 1. In Table 1, carbohydrate includes lactose, galacto-oligosaccharide, dextrin, and monosaccharides.

(2) Preparation of Placebo Sample Solution

As formulated powdered milk for infants not containing galacto-oligosaccharide, a preparation process similar to that for the powdered milk 101 (GOS added) was carried out to prepare a placebo sample solution (powdered milk 102 (placebo)). The formulated powdered milk for infants used in this preparation had the same material composition as that of the formulated powdered milk for infants from which the sample solution (powdered milk 101 (GOS added)) was prepared, except that it did not contain galacto-oligosaccharide and contained maltodextrin at a ratio of 6.2 g/100 g. The powdered milk 101 (GOS added) contained lactose derived from galacto-oligosaccharide liquid sugar, galacto-oligosaccharide and monosaccharides for a total of 4.7 g/100 g, and the powdered milk 101 (GOS added) and powdered milk 102 (placebo) had the same quantity of carbohydrate.

(3) Preparation of Galacto-Oligosaccharide Standard Test Solution

Into a 50-ml measuring flask, galacto-oligosaccharide liquid sugar (Oligomate 55N: Yakult Chemical Industry) was weighed so that the content of galacto-oligosaccharide liquid sugar would become 2.0 g/100 ml, after which precisely 1 ml of aqueous solution containing internal reference substance by 1% was added and then distilled water was added to make the total volume 50 ml, to obtain standard test solution (OM55N).

(4) Preparation of Maltodextrin Standard Test Solution

Into a 50-ml measuring flask, the maltodextrin liquid sugar used for manufacturing the aforementioned formulated powdered milk for infants (high maltose syrup) was weighed so that the content of maltodextrin solution would become 2.0 g/100 ml, after which precisely 1 ml of aqueous solution containing internal reference substance by 1% was added and then distilled water was added to make the total volume 50 ml, to obtain standard test solution (maltodextrin).

(5) Filtering

The test solution, placebo test solution, galacto-oligosaccharide standard test solution, and maltodextrin standard test solution were filtered through a 0.45-μm filter and the filtered solution was analyzed under the HPLC conditions shown below.

TABLE 1

Nutritional Components of Formulated Powdered Milk for Infants (per 100 g)

| Energy | 515 kcal | Vitamin K | 13 μg | α-linolenic acid | 0.4 g |
|---|---|---|---|---|---|
| Protein | 11.9 g | Niacin | 4 mg | Docosahexaenoic acid (DHA) | 80 mg |
| Fat | 27.7 g | Folic acid | 60 μg | Phospholipid | 230 mg |
| Carbohydrate | 55.6 g | Pantothenic acid | 4 mg | Cystine | 190 mg |
| Sodium | 140 mg | β-carotene | 40 μg | Taurine | 25 mg |
| Ash | 2.4 g | Linoleic acid | 3.3 g | Nucleotide | 8 mg |
| Vitamin A | 420 μg | Calcium | 380 mg | Lactoferrin | 100 mg |
| Vitamin B1 | 0.4 mg | Phosphorous | 210 mg | β-lactoglobulin | 0.2 to 0.8 g |
| Vitamin B2 | 0.6 mg | Iron | 7 mg | Water | 2.4 g |
| Vitamin B6 | 0.3 mg | Potassium | 480 mg | | |
| Vitamin B12 | 1.5 μg | Magnesium | 40 mg | | |
| Vitamin C | 60 mg | Chlorine | 320 mg | | |
| Vitamin D | 7 μg | Zinc | 3 mg | | |
| Vitamin E | 4.5 mg | Copper | 320 μg | | |

Galacto-oligosaccharide 2.3 g (Sugars contained are listed below.)
Disaccharides Galβ1-3Glc, Galβ1-2Glc, Galβ1-6Glc,
Trisaccharides Galβ1-6 Galβ1-4Glc, Galβ1-4 Galβ1-4Glc
Tetrasaccharides and higher Galβ1-6 Galβ1-4 Galβ1-4Glc, Galβ1-4 Galβ1-4 Galβ1-4Glc (6) HPLC Analysis
Column: GPC (KS-802) (8.0×300 mm)
Eluent: Distilled water
Flow rate: 0.5 ml/min
Detector: RI detector (Shodex SE-201)
Column temp: 80° C.

Figure 1:
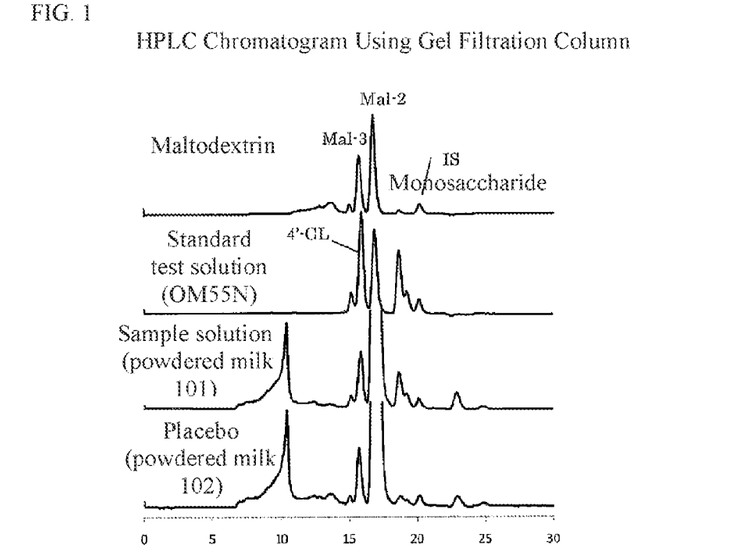
FIG. 1 HPLC chromatogram using a gel filtration column

The results were that, as shown in FIG. 1, the trisaccharide (maltotriose: Mal-3) contained in the maltodextrin and trisaccharide 4'-GL contained in the standard test solution (OM55N) eluted from the column after the same retention time, and the gel filtration chromatography found overlapping peaks of the maltotriose in maltodextrin and 4'-GL in galacto-oligosaccharide and failed to quantify 4'-GL.

Example 1

PMP Derivative—HPLC Reverse-Phase Chromatogram Using C30 Column

Sample solution of formulated powdered milk for infants, placebo sample solution, galacto-oligosaccharide standard test solution and maltodextrin standard test solution were prepared in the same manner as in Comparative Example 1. The galacto-oligosaccharide standard test solution was further diluted with distilled water to prepare a 10-times diluted solution, 20-times diluted solution, and 40-times diluted solution. The concentrations of galacto-oligosaccharide liquid sugar in the diluted solutions were 0.2 g/100 ml, 0.1 g/100 ml and 0.05 g/100 ml, respectively.

(1) PMP Derivatization

Into a threaded-mouth test tube, 100 μl each of sample solution, galacto-oligosaccharide standard test solution, and maltodextrin standard test solution was measured and then 100 μl of 0.6 M NaOH aqueous solution was added and the mixture was agitated. Next, 200 μl of 0.5 M PMP methanol solution was added and the mixture was agitated. The agitated mixture was heated at 70° C. for 30 minutes to be PMP-derivatized. After having been cooled to room temperature, the mixture was turned mildly acidic by adding 0.7 ml of 0.1 M HCl aqueous solution, followed by chloroform-based extraction to remove excess reagent. To be specific, approx. 1 ml of chloroform was added and the mixture was agitated for at least 30 seconds and then centrifuged at 2500 rpm for 5 minutes, to remove the chloroform constituting the bottom layer. The same operation was repeated twice. The water layer was filtered through a 0.45-μm filter and the filtered mixture was analyzed under the HPLC conditions shown below.

(2) HPLC Analysis Conditions
Column: Develosil RPAQUEOUS (4.6×250 mm) (C30)
Eluent: Potassium phosphate buffer solution (pH6)/CH$_3$CN (80/20)
Flow rate: 1.0 ml/min
Detection: UV245 nm
Column temp: 35° C.

Figure 2:
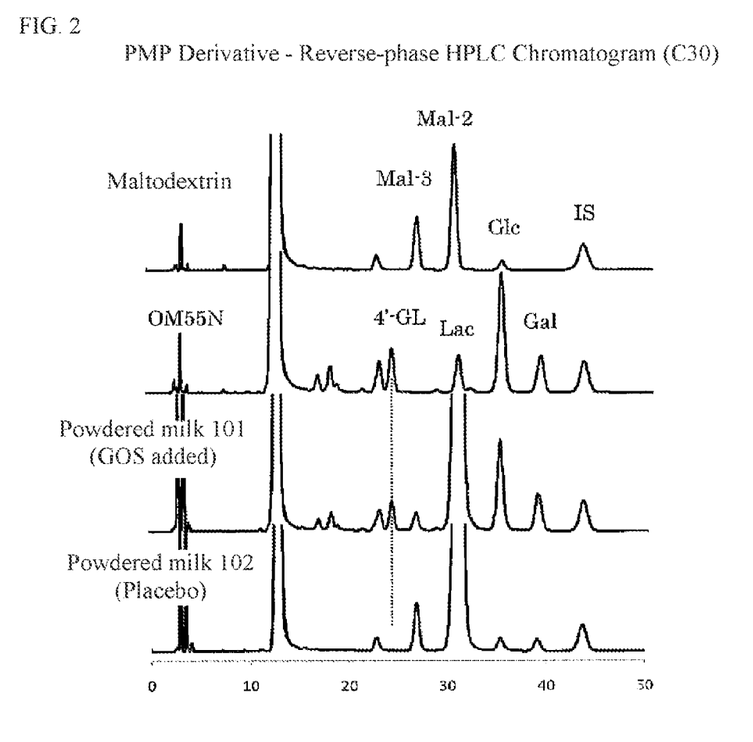
FIG. 2 PMP derivative reverse-phase HPLC chromatogram (C30)

The results were that, as shown by the dotted line in FIG. 2, the peak of 4'-GL detected in the sample solution (powdered milk 101) was not detected in the placebo sample solution (powdered milk 102) and, it was confirmed that, by putting the PMP-derivatized solution through high-performance liquid chromatography using a C30 reverse-phase chromatography column, 4'-GL and maltotriose could be separated.

(3) Calculation of Galacto-Oligosaccharide Content

The diluted solutions prepared from the galacto-oligosaccharide standard test solution were put through HPLC under the same conditions as shown above and, by using the area ratio of internal reference substance and 4'-GL, a calibration curve of galacto-oligosaccharide liquid sugar was obtained. The results of HPLC analysis are shown in Table 2.

TABLE 2

Area Ratios of Internal reference substance and 4'-GL in Galacto-oligosaccharide Standard Test Solutions

| Galacto-oligosaccharide liquid sugar (g/100 ml) | Area | | Area ratio |
| | 4'-GL | Internal reference substance | 4'-GL/Internal reference substance |
| --- | --- | --- | --- |
| 0.05 | 170632 | 806079 | 0.212 |
| 0.10 | 325278 | 807574 | 0.403 |
| 0.20 | 634573 | 799116 | 0.794 |

When a calibration curve was obtained by the least squares method, with x representing the content of galacto-oligosaccharide liquid sugar and y representing the area ratio, the calibration curve was expressed by y=3.9909x. The area ratio of internal reference substance and 4'-GL in the sample solution (0.5526) was assigned to y of this calibration curve and the quantity of galacto-oligosaccharide in the sample was calculated by considering the dilution ratio, etc., of sample solutions (Table 3). To be specific, assigning y=0.5526 to the calibration curve y=3.9909x gave 0.138 (g/100 ml) as x (concentration of galacto-oligosaccharide liquid sugar in the sample solution). Since the sample solution was prepared by diluting the dissolved milk five times, the quantity of galacto-oligosaccharide liquid sugar in the dissolved milk was given as 0.138×5=0.690 (g/100 ml). Since the solid content in the liquid sugar was 75% and the content of galacto-oligosaccharide in the solids was 56.4%, the content of galacto-oligosaccharide in the dissolved milk was given as 0.690×0.75×0.564=0.292 (g/100 ml). Since the concentration of formulated powdered milk for infants in the dissolved milk was 2.6 g/20 ml, 100 ml of dissolved milk contained 13 g of formulated powdered milk for infants, which in turn contained 0.292 g/100 ml of galacto-oligosaccharide, meaning that galacto-oligosaccharide was contained by 2.25 g/100 g per 100 g of formulated powdered milk for infants, which roughly agrees with the blended quantity of galacto-oligosaccharide (2.3 g/100 g).

TABLE 3

Contents of Galacto-oligosaccharide Calculated Using Calibration Curve

| Area | | Area ratio 4'-GL/ Internal reference substance | Quantity of galacto-oligosaccharide liquid sugar | | Quantity of galacto-oligosaccharide | |
| 4'-GL | Internal reference substance | | Sample solution | Dissolved milk | Dissolved milk | Powdered milk |
| --- | --- | --- | --- | --- | --- | --- |
| 434894 | 786975 | 0.5526 | 0.138 g/100 ml | 0.690 g/100 ml | 0.292 g/100 ml | 2.25 g/100 g |

Comparative Example 2

PMP Derivative—Reverse-Phase HPLC Chromatogram Using C8, C18 Columns

Formulated powdered milk for infants containing galacto-oligosaccharide liquid sugar (Oligomate 55N: Yakult Chemical Industry) at a ratio of 2.3 g/100 g based on galacto-oligosaccharide content as well as maltodextrin at a ratio of 1.5 g/100 g was weighed and precisely 5 g of it was weighed and dissolved by adding a small amount of warm water, after which the dissolved formulated powdered milk was let stand until it reached room temperature. Precisely 1 ml of aqueous solution containing internal reference substance by 1% was added, after which distilled water was added to make the total volume 50 ml to obtain a sample solution (powdered milk 101 (GOS added)).

Also, as formulated powdered milk for infants not containing galacto-oligosaccharide, a preparation process similar to that for the powdered milk 101 (GOS added) was carried out to prepare a placebo sample solution (powdered milk 102 (placebo)). The formulated powdered milk for infants used in this preparation had the same material composition as that of the formulated powdered milk for infants from which the sample solution (powdered milk 101 (GOS added)) was prepared, except that it did not contain galacto-oligosaccharide and contained maltodextrin at a ratio of 6.2 g/100 g.

Into a 50-ml measuring flask, galacto-oligosaccharide liquid sugar was weighed so that the content of galacto-oligosaccharide would become 3.0 g/100 ml, after which precisely 1 ml of aqueous solution containing internal reference substance by 1% was added and then distilled water was added to make the total volume 50 ml, to obtain a galacto-oligosaccharide standard test solution.

Into a 50-ml measuring flask, the maltodextrin liquid sugar used for manufacturing the aforementioned formulated powdered milk for infants (high maltose syrup) was weighed so that the content of maltodextrin solution would become 2.0 g/100 ml, after which precisely 1 ml of aqueous solution containing internal reference substance by 1% was added and then distilled water was added to make the total volume 50 ml, to obtain a standard test solution (maltodextrin).

PMP Derivatization

Into a threaded-mouth test tube, 100 μl each of sample solution, galacto-oligosaccharide standard test solution, and maltodextrin standard test solution was measured and then 100 μl of 0.6 M NaOH aqueous solution was added and the mixture was agitated. Next, 200 μl of 0.5 M PMP methanol solution was added and the mixture was agitated. The agitated mixture was heated at 70° C. for 30 minutes to be PMP-derivatized. After having been cooled to room temperature, the mixture was turned mildly acidic by adding 0.7 ml of 0.1 M HCl aqueous solution, followed by chloroform-based extraction to remove excess reagent. To be specific, approx. 1 ml of chloroform was added and the mixture was agitated for at least 30 seconds and then centrifuged at 2500 rpm for 5 minutes, to remove the chloroform constituting the bottom layer. The same operation was repeated twice. The water layer was filtered through a 0.45-μm filter and the filtered mixture was analyzed under the two HPLC conditions shown below.

HPLC Analysis Conditions (1) HPLC Using C18 Column
  Column: Inertsil ODS-3 (4.6×250 mm) (C18 reverse-phase column)
  Eluent: Potassium phosphate buffer solution (pH6)/CH$_3$CN (80/20)
  Flow rate: 1.0 ml/min
  Detection: UV245 nm
  Column temp: 35° C.

(2) HPLC Using C8 Column
  Column: Imtakt UK-8 (4.6×150 mm) (C8 reverse-phase column)
  Eluent: Potassium phosphate buffer solution (pH6)/CH$_3$CN (80/20)
  Flow rate: 1.0 ml/min
  Detection: UV245 nm
  Column temp: 35° C.

Figure 3:
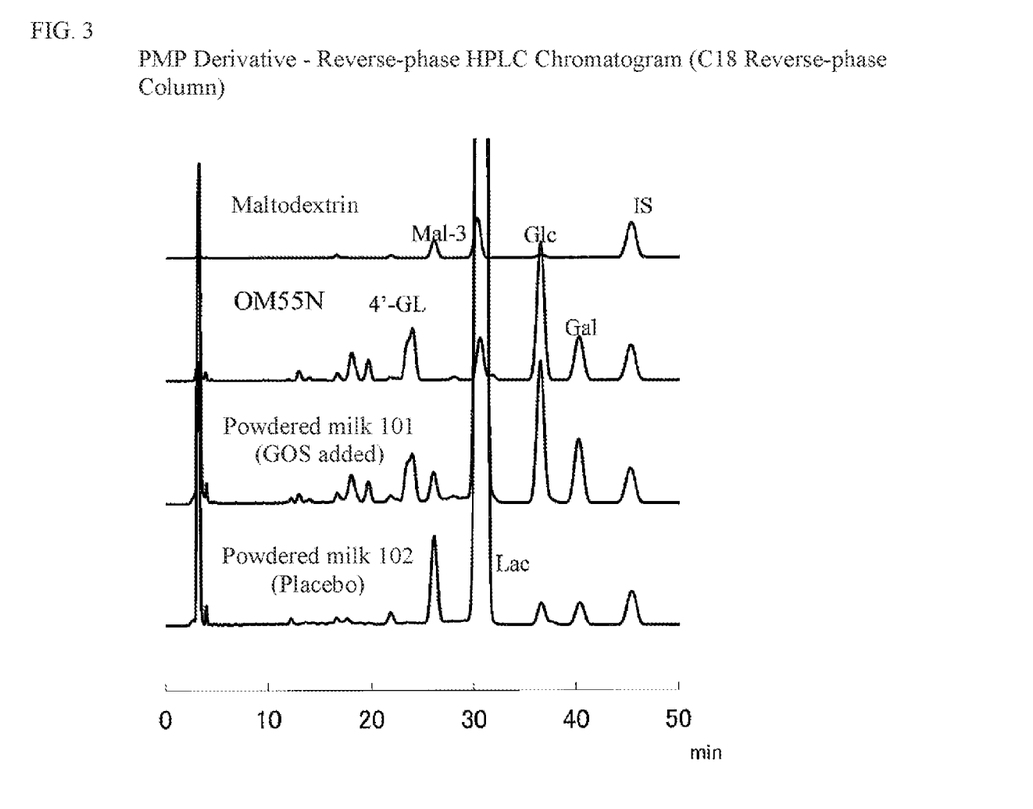
FIG. 3 PMP derivative reverse-phase HPLC chromatogram (C18 reverse-phase column)

The results were that, although 4'-GL and maltotriose (Mal-3) had separated in the C18 reverse-phase chromatography column, the peaks of 4'-GL and other galacto-oligosaccharide components overlapped and 4'-GL could not be separated. To be specific, as shown in FIG. 3, the results of the galacto-oligosaccharide standard test solution (OM55N) and sample solution (powdered milk 101) were such that the peak of 4'-GL overlapped with the peak of other substances on the left side, showing a steplike peak.

Figure 4:
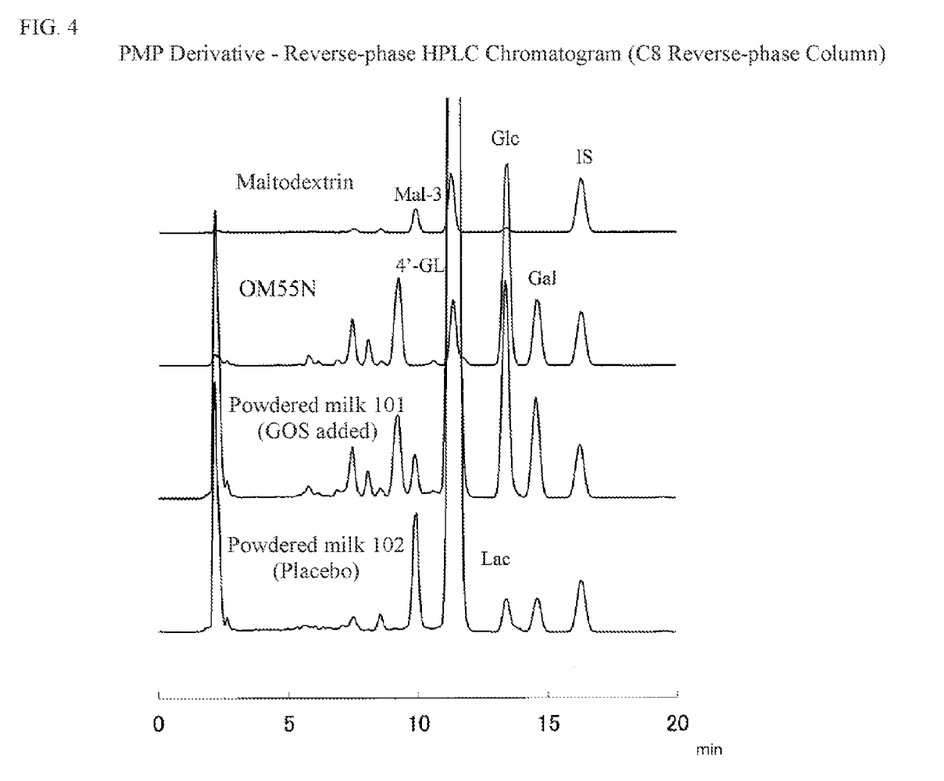
FIG. 4 PMP derivative reverse-phase HPLC chromatogram (C8 reverse-phase column)

When the C8 reverse-phase chromatography column was used, 4'-GL and maltotriose (Mal-3) had separated but the peaks of 4'-GL and other galacto-oligosaccharide components overlapped and separation could not be achieved (FIG. 4). To be specific, the comparison with the analysis using the C30 reverse-phase chromatography column (FIG. 2) found that, while the peak of other galacto-oligosaccharide components is present to the immediate left of 4'-GL in FIG. 2, this peak overlaps with the peak of 4'-GL to create a higher combined peak in FIG. 4. These results suggest that 4'-GL cannot be separated or quantified using either the C8 column or C18 column.

Example 2

Examination of Eluent in HPLC

Sample solutions (powdered milk 101 (GOS added), powdered milk 102 (placebo)), galacto-oligosaccharide standard test solution and maltodextrin standard test solution were prepared in the same manner as in Comparative Example 2 and then PMP-derivatized in the same manner as in Comparative Example 2 and analyzed under the six HPLC conditions as shown below, respectively.

(1) HPLC Conditions at Buffer Solution pH4
  Column: Develosil RPAQUEOUS (4.6×250 mm)
  Eluent: Potassium phosphate buffer solution (pH4)/CH$_3$CN (78/22)
  Flow rate: 1.0 ml/min
  Detection: UV245 nm
  Column temp: 35° C.

(2) HPLC Conditions at Buffer Solution pH5
  Column: Develosil RPAQUEOUS (4.6×250 mm)
  Eluent: Potassium phosphate buffer solution (pH5)/CH$_3$CN (79/21)
  Flow rate: 1.0 ml/min
  Detection: UV245 nm
  Column temp: 35° C.

(3) HPLC Conditions at Buffer Solution pH7
  Column: Develosil RPAQUEOUS (4.6×250 mm)
  Eluent: Potassium phosphate buffer solution (pH7)/CH$_3$CN (81/19)
  Flow rate: 1.0 ml/min
  Detection: UV245 nm
  Column temp: 35° C.

(4) HPLC Conditions at Buffer Solution pH7
  Column: Develosil RPAQUEOUS (4.6×250 mm)
  Eluent: Potassium phosphate buffer solution (pH7)/CH$_3$CN (82/18)

Flow rate: 1.0 ml/min
Detection: UV245 nm
Column temp: 35° C.

(5) HPLC Conditions at Buffer Solution pH8
Column: Develosil RPAQUEOUS (4.6×250 mm)
Eluent: Potassium phosphate buffer solution (pH8)/ $CH_3CN$ (82/18)
Flow rate: 1.0 ml/min
Detection: UV245 nm
Column temp: 35° C.

(6) HPLC Conditions at Buffer Solution pH8
Column: Develosil RPAQUEOUS (4.6×250 mm)
Eluent: Potassium phosphate buffer solution (pH8)/ $CH_3CN$ (83/17)
Flow rate: 1.0 ml/min
Detection: UV245 nm
Column temp: 35° C.

Figure 5:
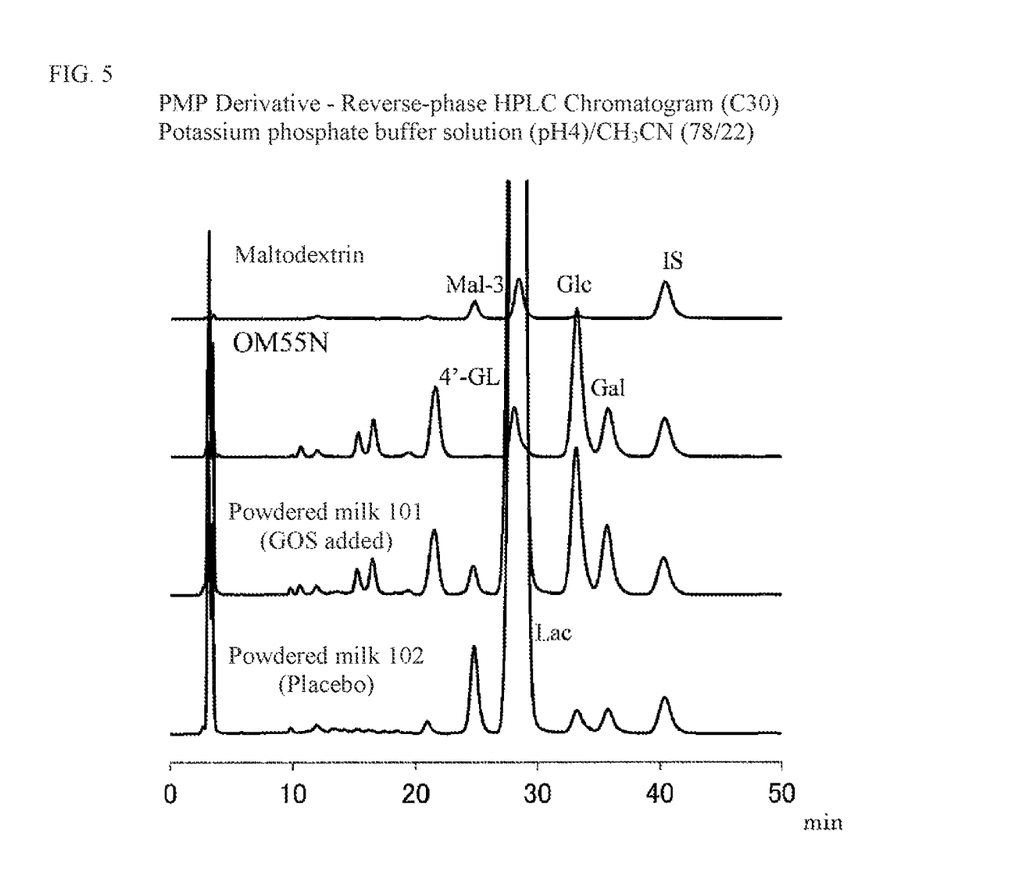
FIG. 5 PMP derivative reverse-phase HPLC chromatogram (C30), potassium phosphate buffer solution (pH4)/CH$_3$CN (78/22)

The results of Example 1 showed that, when potassium phosphate buffer solution of pH6 was used, 4'-GL could be separated and galacto-oligosaccharide could be quantified. On the other hand, as shown in FIGS. 5, 7 to 10, use of potassium phosphate buffer solutions of pH4, 7 and 8 caused the peaks of 4'-GL and other galacto-oligosaccharide components to overlap and 4'-GL could not be separated or quantified as a result. To be specific, while the peak of other galacto-oligosaccharide components is present to the immediate left of 4'-GL in FIG. 2, use of potassium phosphate buffer solution of pH4 resulted in a single peak as shown in the chromatogram of OM55N, indicating that 4'-GL could not be separated (FIG. 5).

Additionally, when eluent containing potassium phosphate buffer solution (pH7) and $CH_3CN$ at a ratio of 81/19 (FIG. 7) was used, the peak of other galacto-oligosaccharide components overlapped with the peak of 4'-GL on its right, as shown in the chromatogram of OM55N, thus making the peak area of 4'-GL larger.

When eluent containing potassium phosphate buffer solution (pH7) and $CH_3CN$ at a ratio of 82/18 was used (FIG. 8), the resulting chromatogram of OM55N does not show a peak to the immediate left of 4'-GL where it should be detected, but this peak overlaps with the peak of 4'-GL instead.

When eluent containing potassium phosphate buffer solution (pH8) and $CH_3CN$ at a ratio of 82/18 was used (FIG. 9) or at a ratio of 83/17 was used (FIG. 10), comparing the chromatogram of OM55N and that of maltodextrin finds that 4'-GL could be separated from maltotriose and other oligosaccharide components; however, comparing the chromatogram of OM55N and that of placebo sample solution (powdered milk 102) finds that the peak of 4'-GL agrees with the peak of other components in the powdered milk 102, thus preventing 4'-GL alone from being separated.

Figure 6:
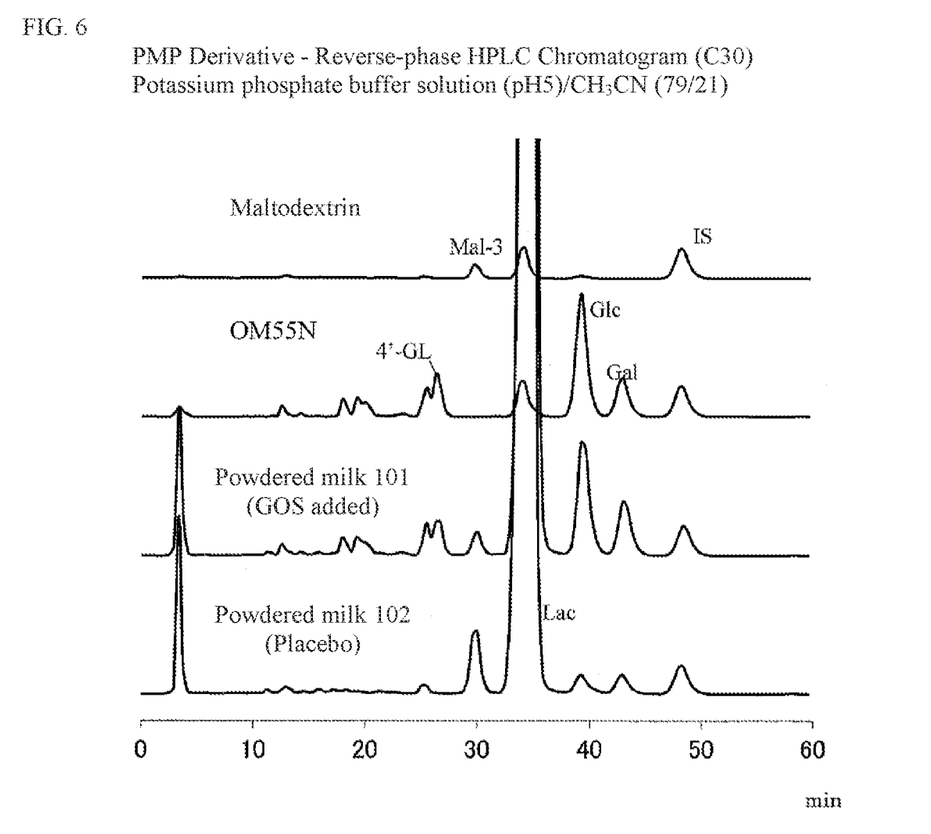
FIG. 6 PMP derivative reverse-phase HPLC chromatogram (C30), potassium phosphate buffer solution (pH5)/CH$_3$CN (79/21)
Figure 7:
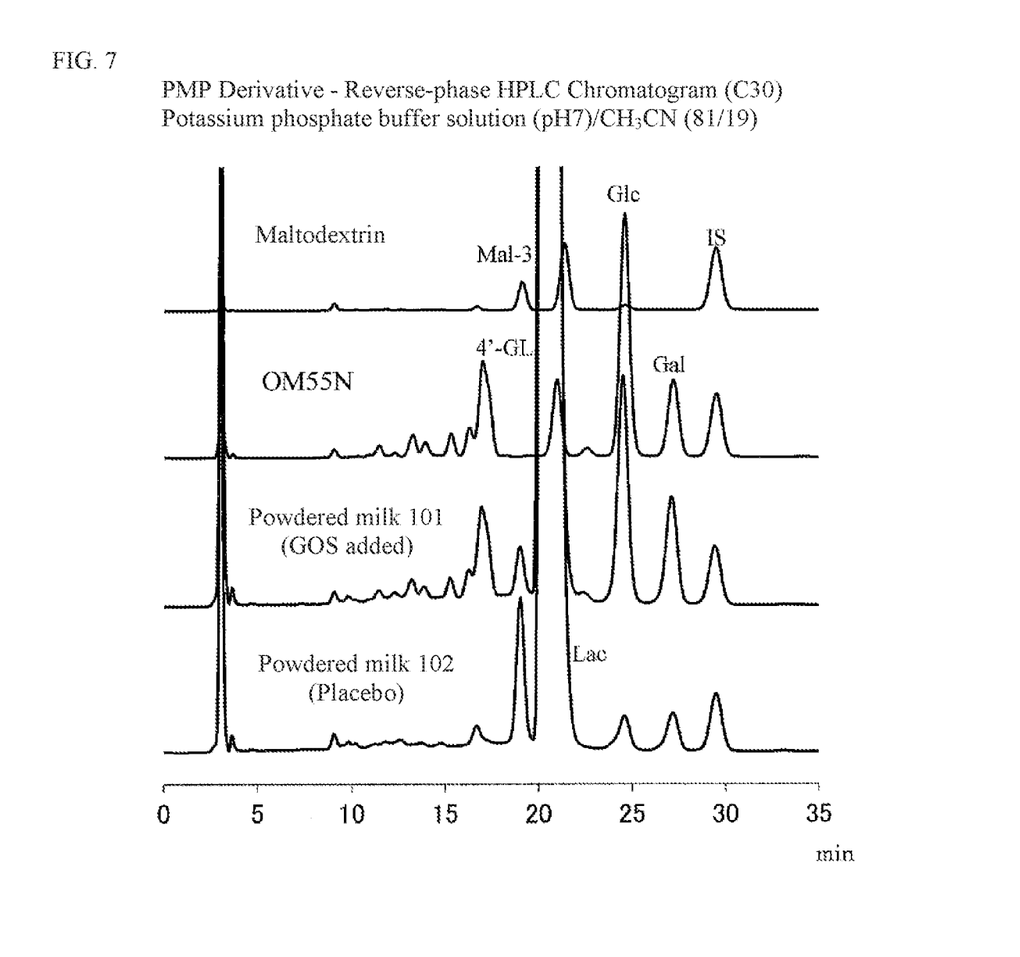
FIG. 7 PMP derivative reverse-phase HPLC chromatogram (C30), potassium phosphate buffer solution (pH7)/CH$_3$CN (81/19)
Figure 8:
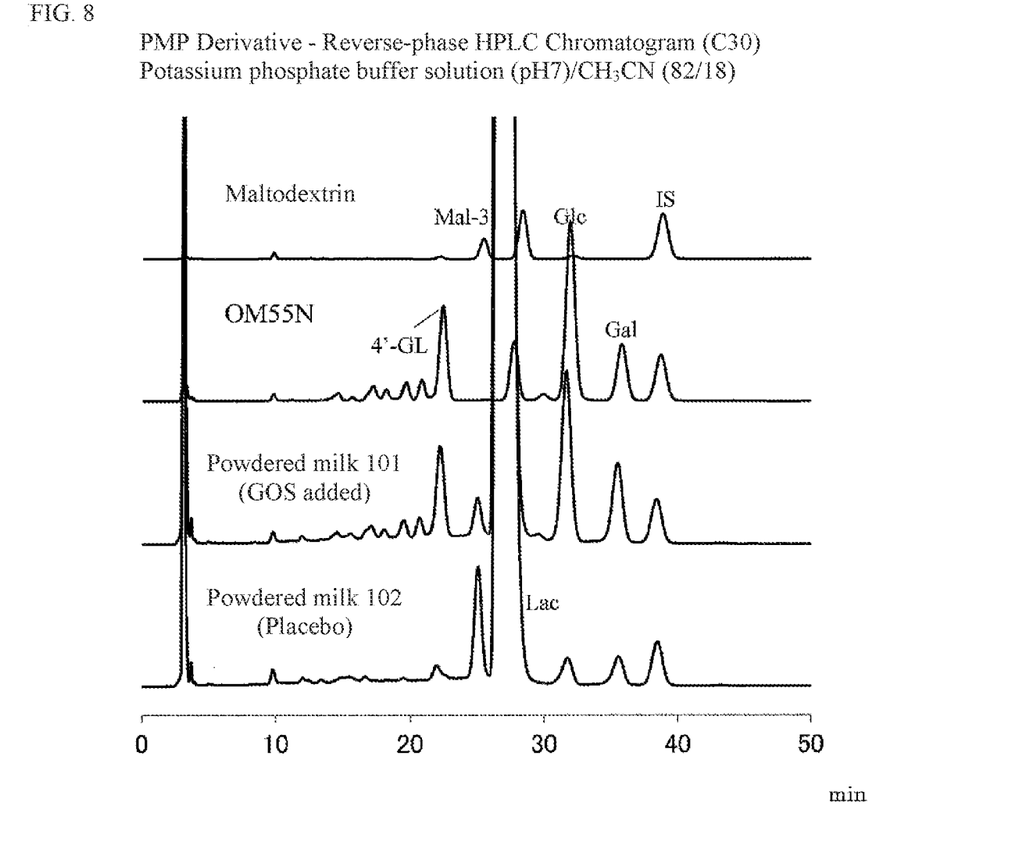
FIG. 8 PMP derivative reverse-phase HPLC chromatogram (C30), potassium phosphate buffer solution (pH7)/CH$_3$CN (82/18)
Figure 9:
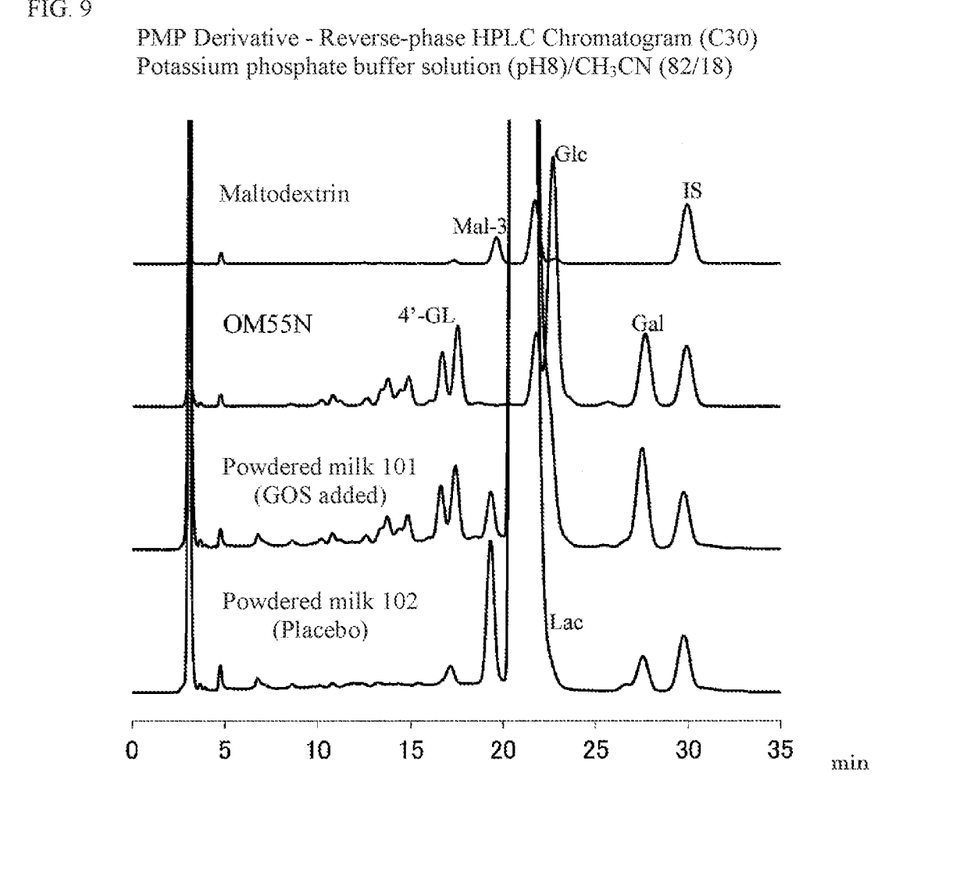
FIG. 9 PMP derivative reverse-phase HPLC chromatogram (C30), potassium phosphate buffer solution (pH8)/CH$_3$CN (82/18)
Figure 10:
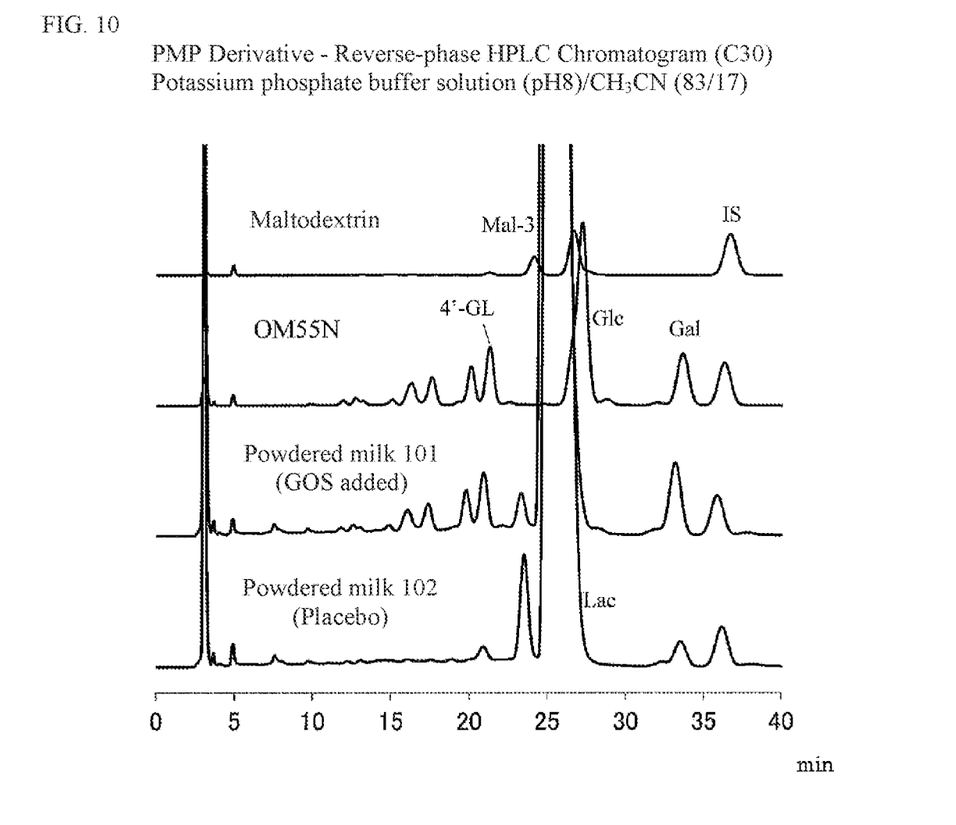
FIG. 10 PMP derivative reverse-phase HPLC chromatogram (C30), potassium phosphate buffer solution (pH8)/CH$_3$CN (83/17)

When eluent containing potassium phosphate buffer solution (pH5) and $CH_3CN$ at a ratio of 79/21 was used (FIG. 6), on the other hand, 4'-GL could be separated from maltotriose and other galacto-oligosaccharide components.

Example 3

PMP Derivative—Reverse-Phase HPLC Chromatogram (C30) of Nutritional Food Sample

The materials shown in Table 4 were mixed to prepare nutritional food. Distilled water was added to 10 g of this nutritional food to make the total volume 50 ml, after which the mixture was centrifuged at 20000 g for 30 minutes and again at 20000 g for 30 minutes. The centrifuged nutritional food had separated into three layers of bottom layer, middle layer and top layer. The middle layer was separated and the separated sample was filtered through a 0.45-μm filter. Separately, as a standard sample, galacto-oligosaccharide standard test solution was prepared using Oligomate 55 (Yakult Chemical Industry) in the same manner as in Comparative Example 1. Into a threaded-mouth test tube, 100 μl each of filtered sample and galacto-oligosaccharide standard test solution was measured and then dried and solidified under reduced pressure. To this, 100 μl of aqueous solution containing internal reference substance by 0.02% was added and then 200 μl of 0.5 M PMP methanol solution was added, and the mixture was agitated. Next, the mixture was heated at 70° C. for 30 minutes to be PMP-derivatized, and analyzed under the HPLC conditions shown below.

TABLE 4

Composition of Nutritional Food

| | Blended quantity per 100 mL (g) |
|---|---|
| Calcium caseinate | 3.4409 |
| Sodium caseinate | 2.5806 |
| Mixed oil | 02151 |
| Maltodextrin | 10.1075 |
| Granulated sugar | 2.4731 |
| Indigestible dextrin | 0.6000 |
| Oligomate 55 | 0.4086 |
| Vitamin mixture | 0.1000 |
| Sodium ascorbic acid | 0.0630 |
| Magnesium sulfate (crystalline heptahydrate) | 0.2495 |
| Potassium chloride (anhydrous) | 0.2043 |
| Sodium carbonate (anhydrous) | 0.1290 |
| Dipotassium hydrogen phosphate (anhydrous) | 0.0400 |
| Mineral yeast mixture | 0.0418 |
| Emulsifier (Sunsoft) | 0.2000 |
| Carrageenan | 0.0400 |
| Crystalline cellulose | 0.0301 |
| Defoaming silicon | 0.0140 |
| Flavoring agent | 0.7633 |
| Material water | 83.4624 |
| Total | 106.9913 |

HPLC Analysis Conditions
Column: Develosil RPAQUEOUS (4.6×250 mm)
Eluent: Potassium phosphate buffer solution (pH6)/ $CH_3CN$ (80/20)
Flow rate: 1.0 ml/min
Detection: UV245 nm
Column temp: 35° C.

Figure 11:
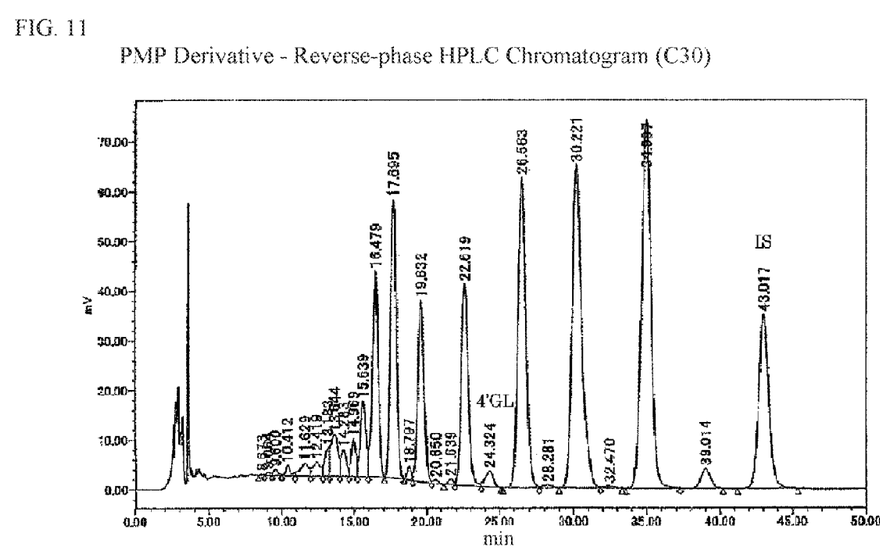
FIG. 11 PMP derivative reverse-phase HPLC chromatogram (C30)

The results are that, as shown in FIG. 11, the peak of 4'-GL appeared after 24.324 minutes of retention time, revealing that it was separated from other components contained in the sample. It should be noted that the appearance of the 4'-GL peak after 24.324 minutes of retention time was confirmed by analyzing the galacto-oligosaccharide standard test solution under the same HPLC analysis conditions.

INDUSTRIAL FIELD OF APPLICATION

According to the detection and quantification method proposed by the present invention, galacto-oligosaccharide and other components in the sample can be separated with ease and at low cost to allow for accurate quantification of galacto-oligosaccharide, which enables accurate management of galacto-oligosaccharide quantity in the sample as well as accurate acquisition and display of various effectiveness test data, etc.

The invention claimed is:

1. A method for detecting galacto-oligosaccharide, which is a method for detecting galacto-oligosaccharide in a sample containing galacto-oligosaccharide and dextrin, comprising the steps of:
   causing the sample to react with a derivatizing reagent to derivatize the dextrin and galacto-oligosaccharide in the sample, and then
   separating and detecting galacto-oligosaccharide components in the sample by high-performance liquid chromatography using a C30 reverse-phase chromatography column.

2. A method for detecting galacto-oligosaccharide according to claim 1, wherein a mixed liquid of buffer solution and polar organic solvent is used as an eluent for high-performance liquid chromatography.

3. A method for detecting galacto-oligosaccharide according to claim 2, wherein a buffer solution of pH5 to 6 is used as the buffer solution.

4. A method for detecting galacto-oligosaccharide according to claim 2, wherein a mixing ratio (vol/vol) of buffer solution and polar organic solvent in the mixed liquid is in a range of 79/21 to 80/20 based on buffer solution/polar organic solvent.

5. A method for detecting galacto-oligosaccharide according to claim 2, wherein, for the buffer solution used in preparing the mixed liquid, at least one type selected from potassium phosphate buffer solution, potassium citrate buffer solution, ammonium formate buffer solution, and potassium acetate buffer solution is used, and for the polar organic solvent, at least one type selected from acetonitrile, methanol, ethanol, propanol, and butanol is used.

6. A method for detecting galacto-oligosaccharide according to claim 1, wherein the sample containing galacto-oligosaccharide and dextrin is a beverage or food.

7. A method for detecting galacto-oligosaccharide according to claim 1, wherein the galacto-oligosaccharide components to be separated are 4'-galactosyl lactose.

8. A method for detecting galacto-oligosaccharide according to claim 1, wherein, for the derivatizing reagent, one type selected from 1-phenyl-3-methyl-5-pyrazolone, 2-aminopyridine, 2-aminobenzamide, 3-aminoquinone, ethyl 4-amino benzoate, butyl 4-amino benzoate, and 4-trimethyl ammonium aniline is used.

9. A method for detecting galacto-oligosaccharide according to claim 1, wherein the C30 reverse-phase chromatography column has a stationary phase containing cis alkyl groups having double bonds.

* * * * *